United States Patent
Krill et al.

(10) Patent No.: US 11,299,449 B2
(45) Date of Patent: Apr. 12, 2022

(54) PROCESS FOR PREPARING MMA IN HIGH YIELDS

(71) Applicant: Röhm GmbH, Darmstadt (DE)

(72) Inventors: Steffen Krill, Muehltal (DE); Florian Zschunke, Frankfurt (DE); Belaid Ait Aissa, Darmstadt (DE); Marcel Treskow, Mobile, AL (US)

(73) Assignee: Röhm GmbH, Darmstadt (DE)

( * ) Notice: Subject to any disclaimer, the term of this patent is extended or adjusted under 35 U.S.C. 154(b) by 0 days.

(21) Appl. No.: 17/250,260

(22) PCT Filed: Jun. 7, 2019

(86) PCT No.: PCT/EP2019/064957
§ 371 (c)(1),
(2) Date: Dec. 22, 2020

(87) PCT Pub. No.: WO2020/001957
PCT Pub. Date: Jan. 2, 2020

(65) Prior Publication Data
US 2021/0269385 A1    Sep. 2, 2021

(30) Foreign Application Priority Data
Jun. 26, 2018 (EP) ..................... 18179702

(51) Int. Cl.
C07C 67/08 (2006.01)
C07C 67/54 (2006.01)
(Continued)

(52) U.S. Cl.
CPC ............. *C07C 67/44* (2013.01); *C07C 67/08* (2013.01); *C07C 67/317* (2013.01);
(Continued)

(58) Field of Classification Search
None
See application file for complete search history.

(56) References Cited

U.S. PATENT DOCUMENTS 2,562,849 A * 7/1951 Whetstone ............ C07C 67/333
                                                  560/205
2,577,445 A * 12/1951 Bortnick ............... C07C 45/673
                                                  568/483
(Continued)

FOREIGN PATENT DOCUMENTS

DE    1 279 015       10/1968
JP    S5212127    *   1/1977    ............ C07C 67/327
(Continued)

OTHER PUBLICATIONS

English language translation of JP 52012127, published Jan. 29, 1977 (Year: 1977).*
(Continued)

*Primary Examiner* — Amy G Bonaparte
(74) *Attorney, Agent, or Firm* — Grüneberg and Myers PLLC

(57) ABSTRACT

A process for preparing methyl methacrylate by direct oxidative esterification of methacrolein has elevated yields compared to known processes. Methyl methacrylate (MMA) is used in large amounts for preparing polymers and copolymers with other polymerizable compounds. In addition, methyl methacrylate is an important synthesis unit for a variety of specialty esters based on methacrylic acid (MAA), which can be produced by transesterification with the appropriate alcohol. There is consequently a great interest in very simple, economic, and environmentally friendly processes for preparing methyl methacrylate. A superior workup of the reactor output from the oxidative esterification of methacrolein allows specific by-products to be isolated and then
(Continued)

additionally converted to alkyl methacrylates, especially to MMA.

20 Claims, 1 Drawing Sheet

(51) Int. Cl.
*C07C 67/58* (2006.01)
*C07C 67/39* (2006.01)
*C07C 67/327* (2006.01)
*C07C 69/54* (2006.01)
*C07C 67/44* (2006.01)
*C07C 67/317* (2006.01)

(52) U.S. Cl.
CPC ............ *C07C 67/327* (2013.01); *C07C 67/39* (2013.01); *C07C 67/54* (2013.01); *C07C 67/58* (2013.01); *C07C 69/54* (2013.01)

(56) References Cited

U.S. PATENT DOCUMENTS

| | | | |
|---|---|---|---|
| 3,227,746 A | 1/1966 | Knörr et al. | |
| 3,642,907 A * | 2/1972 | Schenach | C07C 45/60 568/386 |
| 5,969,178 A | 10/1999 | Okamoto et al. | |
| 7,012,039 B2 | 3/2006 | Watanabe et al. | |
| 9,617,199 B2 | 4/2017 | Krill et al. | |
| 9,890,105 B2 | 2/2018 | Krill et al. | |
| 9,963,417 B2 | 5/2018 | Krill et al. | |
| 10,273,201 B2 | 4/2019 | Krill et al. | |
| 10,301,251 B2 | 5/2019 | Groemping et al. | |
| 10,457,626 B2 | 10/2019 | Krill et al. | |
| 10,479,754 B2 | 11/2019 | Krill et al. | |
| 10,766,847 B2 | 9/2020 | Krill et al. | |
| 2016/0068464 A1 * | 3/2016 | Krill | C07C 67/39 560/208 |
| 2016/0251301 A1 * | 9/2016 | Krill | C07C 67/39 560/208 |
| 2018/0001307 A1 * | 1/2018 | Lygin | B01J 23/688 |
| 2018/0251419 A1 * | 9/2018 | Groemping | C07C 67/54 |

FOREIGN PATENT DOCUMENTS

| | | | | |
|---|---|---|---|---|
| WO | 2013/184345 | 12/2013 | | |
| WO | 2014/170223 | 10/2014 | | |
| WO | WO-2016113106 A1 * | 7/2016 | ............. | B01J 23/52 |
| WO | 2016/166525 | 10/2016 | | |
| WO | WO-2017046110 A1 * | 3/2017 | ............. | C07C 67/39 |

OTHER PUBLICATIONS

International Search Report dated Sep. 13, 2019 in PCT/EP2019/064957, with English translation, 5 pages.
Written Opinion dated Sep. 13, 2019 in PCT/EP2019/064957.
U.S. Pat. No. 9,617,199, Apr. 11, 2017, 2016/0251301, Krill et al.
U.S. Pat. No. 9,963,417, May 8, 2018, 2016/0280628, Krill et al.
U.S. Pat. No. 10,301,251, May 28, 2019, 2018/0251419, Groemping et al.
U.S. Pat. No. 10,479,754, Nov. 19, 2019, 2018/0251418, Krill et al.
U.S. Appl. No. 16/611,546, filed Nov. 7, 2019, Lygin et al.
U.S. Appl. No. 16/637,575, filed Feb. 7, 2020, Krill et al.
U.S. Pat. No. 9,890,105, Feb. 13, 2018, 2016/0068464, Krill et al.
U.S. Pat. No. 10,273,201, Apr. 30, 2019, 2018/0050977, Krill et al.
U.S. Pat. No. 10,457,626, Oct. 29, 2019, 2019/0077742, Krill et al.
U.S. Pat. No. 10,766,847, Sep. 8, 2020, 2019/0112255, Krill et al.

* cited by examiner

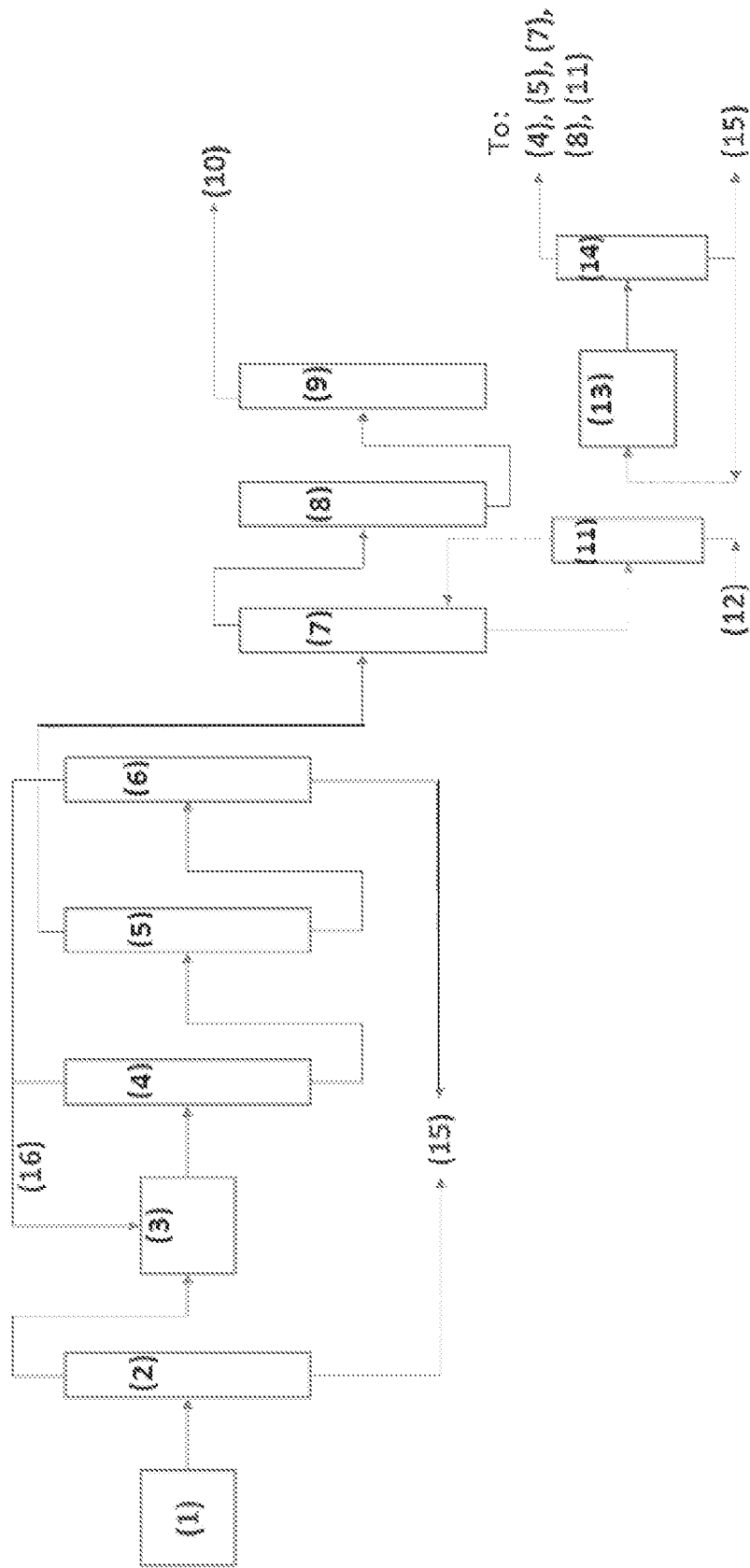

PROCESS FOR PREPARING MMA IN HIGH YIELDS

CROSS-REFERENCE TO RELATED APPLICATIONS

This application is a National Stage entry under § 371 of International Application No. PCT/EP2019/064957, filed on Jun. 7, 2019, and which claims the benefit of European Application No. 18179702.8, filed on Jun. 26, 2018. The content of each of these applications is hereby incorporated by reference in its entirety.

FIELD OF THE INVENTION

The present invention relates to a process for preparing methyl methacrylate by direct oxidative esterification of methacrolein having elevated yields compared to the prior art. Methyl methacrylate is used in large amounts for preparing polymers and copolymers with other polymerizable compounds. In addition, methyl methacrylate is an important synthesis unit for a variety of specialty esters based on methacrylic acid (MAA) which can be produced by transesterification with the appropriate alcohol. There is consequently a great interest in very simple, economic and environmentally friendly processes for preparing this starting material.

More particularly, the present invention relates to an optimized workup of the reactor output from the oxidative esterification of methacrolein, by means of which specific by-products can be isolated and then additionally converted to alkyl methacrylates, especially to MMA.

PRIOR ART

Methyl methacrylate (MMA) is currently produced by a variety of processes proceeding from $C_2$, $C_3$ or $C_4$ synthesis units. In one of these processes MMA is obtained by gas-phase oxidation of isobutylene or tert-butanol with atmospheric oxygen over a heterogeneous catalyst to afford methacrolein (MAL) and subsequent oxidative esterification reaction of methacrolein using methanol. This process, developed by ASAHI, is described, inter alia, in publications U.S. Pat. Nos. 5,969,178 and 7,012,039. A particular disadvantage of this process is a very high energy requirement.

Scheme 1 below shows a schematic of the preparation of MMA by what is called the Asahi process proceeding from $C_4$ (isobutene or tert-butanol), with intermediate isolation of MAL and subsequent oxidative esterification (abbreviated to "DOE") of the MAL with methanol to give MMA, with formation of methacrylic acid (MAA) as by-product.

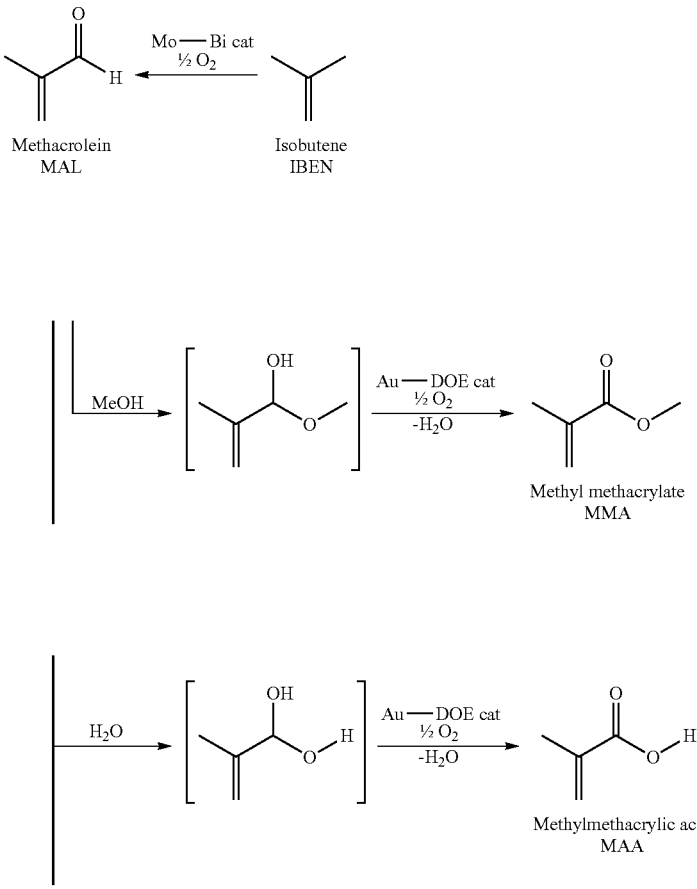

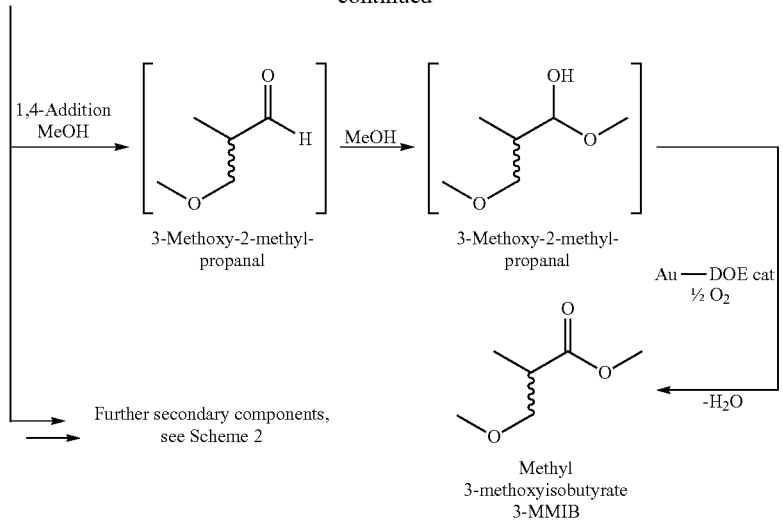

In a development of the process, the methacrolein is obtained from propanal and formalin in the first stage. Such a process is described in WO 2014/170223.

U.S. Pat. No. 5,969,175 describes such a process for oxidative conversion of isobutene or tert-butanol to methacrolein and subsequent oxidative esterification to MMA. In this second stage a liquid mixture of methacrolein and methanol with reduced water content is reacted with molecular oxygen and a palladium catalyst, wherein said catalyst is usually in supported form as a palladium-lead catalyst. In a first distillation stage a mixture of methacrolein and methanol is then removed from the crude product of the oxidative esterification below the top or the column while low-boiling constituents are removed overhead. The MMA-containing bottoms product is then passed into a second distillation stage in which an azeotrope of methanol and saturated hydrocarbons is removed overhead. The bottoms product comprising the crude MMA is sent to a further workup while methanol is Isolated from the overhead fraction by means of a phase separator and a third distillation column and passed back into the reactor. It is to be borne in mind that the methanol can contain relatively large amounts of water on account of the azeotrope formed and must therefore be sent to a dewatering.

As an alternative to this process U.S. Pat. No. 5,969,178 discloses workup in only one column wherein in said column it is imperative that the feed be situated above the column bottom. Low-boiling constituents from the reactor output are removed from this column overhead. Remaining in the column bottom is a mixture of crude MMA and water which is to be sent to a further workup. Via a sidestream whose exact position must first be determined, said position being adjustable by addition of various sieve trays, a mixture of methacrolein and methanol intended for returning into the reactor is finally taken off from the column. U.S. Pat. No. 5,969,178 itself indicates that such a process is difficult to perform on account of a variety of azeotropes. Furthermore, methacrylic acid in particular, which is always present as a by-product, plays an important role. According to this process, despite the silence of U.S. Pat. No. 5,969,178 on this issue, the methacrylic acid would be removed in a manner such that it remains in a phase to be sent for disposal and an isolation would be of only limited attractiveness. However, this means that there is a fall in the overall yield of methacrylic products of this process.

U.S. Pat. No. 7,012,039 discloses a workup of the reactor output from the oxidative esterification which is somewhat of a departure. Here, in a first distillation stage methacrolein is distilled overhead via sieve trays and the aqueous. MMA-containing mixture from the bottom is passed into a phase separator. In said phase separator the mixture is adjusted to a pH of about 2 by addition of sulfuric acid. The separation of the sulfuric-acid-acidified water from the organic/oil phase is then effected by means of centrifuging. This organic phase is separated in a further distillation into high-boiling constituents and an MMA-containing phase withdrawn overhead. The MMA-containing phase is then separated from low-boning constituents in a third distillation. This is even followed by a fourth distillation for final purification.

The problem with this process is the sulfuric acid which needs to be added in large amounts and can have corrosive effects on parts of the plant. Accordingly, these parts, such as the phase separator or else the second distillation column in particular, have to be fabricated from suitable materials. Moreover, U.S. Pat. No. 7,012,039 is silent regarding the handling of the simultaneously generated methacrylic acid or the residual methanol remaining in the product. However, it can be assumed that the former is also removed in the distillation stages, while the methanol can only partly be obtained and returned with the methacrolein, while the remainder is probably lost in the third distillation stage.

WO 2014/170223 describes a similar process to U.S. Pat. No. 7,012,039. The only difference is that in the actual reaction the pH is adjusted in a circuit by addition of a methanolic sodium hydroxide solution. If the process is conducted without pH regulation as described in the two publications cited, there is "acidification" of the reaction. Within a pH range below 7, this leads to increased formation of the acetal of methacrolein, which would have to be removed or hydrolytically cleaved in a complex manner. Moreover, the activity of the oxidation catalyst is dependent on the pH among other factors. Under conditions below pH 7, the catalyst increasingly shows lower activity with falling pH of the reaction matrix, which is undesirable. Another purpose of the pH regulation is additionally to protect the catalyst. Moreover, the removal of the aqueous phase in the phase separation is simpler on account or the salt content.

However, another effect or this is that the methacrylic acid formed is in the form of sodium salt and is later removed and disposed of with the aqueous phase. In the variant of sulfuric acid addition in the phase separation, the free acid is recovered, but at the cost of sodium (hydrogen)sulfate obtained, which can lead to other problems in the disposal.

In principle, and in a summary of the prior art, the oxidative esterification of methacrolein or else acrolein in the presence of methanol as alcohol in general in the direct oxidative esterification of unsaturated aldehydes gives rise to a variety of high-boiling components. These high boilers boil at a higher level compared to methyl methacrylate (MMA), the desired product, and thus have to be separated from MMA in the later isolation of the MMA to produce a suitable purity of the monomer of distinctly greater than 99% by weight. These by-products, especially methacrylic acid, methyl methoxyisobutyrate, dimeric methacrolein (an aldehyde) and the corresponding ester of dimeric methacrolein, form in significant amounts and can have a distinctly adverse effect on the yield of desired MMA. Since they have to be separated from MMA formed, it is likewise necessary to send these substances to a disposal operation, in the simplest case a combustion, a thermal utilization with recovery of steam or a biological degradation in a water treatment plant.

One of the by-products is methacrylic acid, which forms in the DOE reaction in the presence of water, which is typically present in the reactor at a steady-state concentration between 2% and 20% by weight in the course or continuous performance of the reaction. If the DOE reaction is conducted at constant pH, the methacrylic acid as it forms is at least partly neutralized with alkaline or basic auxiliaries, in the simplest case alkali metal compounds.

The reaction likewise forms methoxy isobutyral, the Michael addition product of methanol onto methacrolein. This methoxy isobutyral is reacted under the conditions of the DOE in the presence of an oxygenous gas and methanol, for example, at least partly to give the methyl methoxyisobutyrate (MMIB) as a side reaction. The reaction is alkali-catalysed, i.e. is inevitably formed as a result of the addition of a base which is used to control the pH of the DOE reaction. A general observation is that the formation of methoxy isobutyral and hence the consecutive formation of MMIB becomes more marked with rising pH. According to the catalyst used and according to the chosen steady-state pH of the DOE reaction, between 0.1% and up to 5% of this by-product is formed in the reactor.

The prior art, for example German Auslegeschrift 1279015, Knörr et al, describes how alkyl alkoxypropionates can be thermally and catalytically cleaved to form unsaturated acrylic esters. In this case, pure substances are used as reactants and pure β elimination is described.

In the WO2016166525A1 application, Lucite describes the catalytic, base-induced splitting of methyl methoxyisobutyrate to methanol and methyl methacrylate. In this case, pure substances are used as reactants under protective gas atmosphere at 95° C. However, the conversion is only at a low 37%.

Scheme 2 below shows the reaction matrix (by way of example with ethylene and syngas and formalin to give methacrolein; as described, access to methacrolein proceeding from isobutene or tert-butanol is also possible); In particular, the formation of the MMA target product and the high-boiling by-products MAA, MMIB, DIMAL and DIMAL ester are shown:

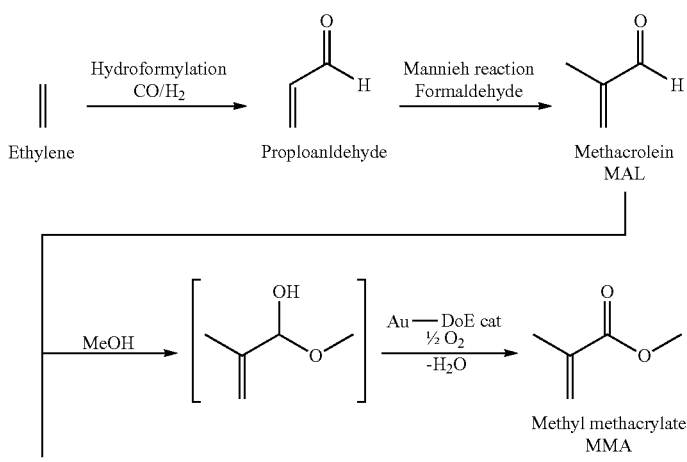

Scheme 2: Reaction matrix of the C2 process for preparing MMA.

-continued

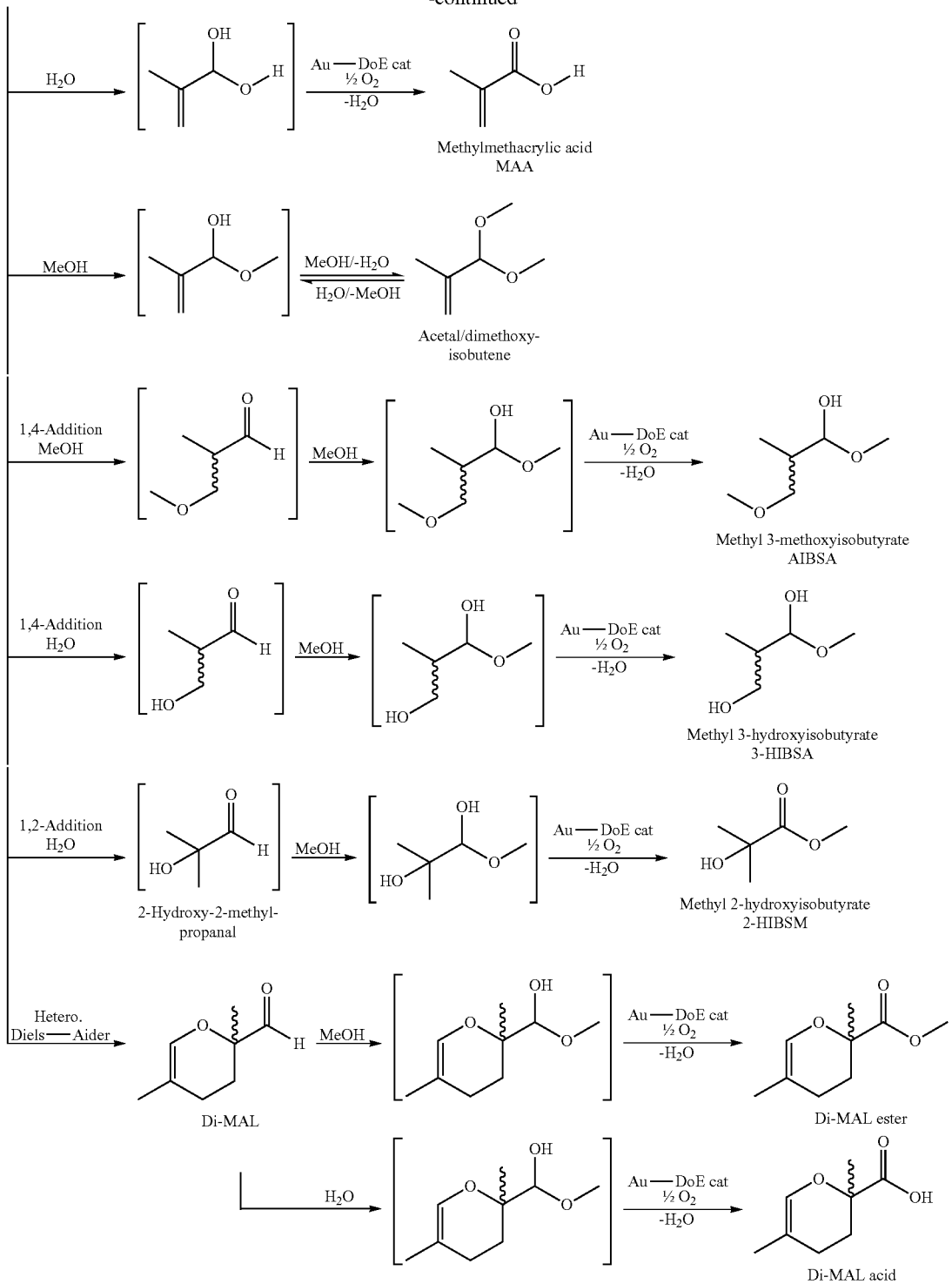

The result in the product matrix of the DOE reaction is a mixture comprising water, methanol, MMA, free methacrylic acid, as well as alkali-neutralized methacrylic acid, for example sodium methacrylate, and the further by-products described in Scheme 2.

In summary, the following aspects of the prior art processes, especially in combination with one another, are in need of improvement:

maximum yield of MMA conversion of the methacrylic acid by-product to methyl methacrylate and isolation conversion of the methyl methoxyisobutyrate (MMIB) by-product to methanol and MMA, and recycling of the methanol formed or the use of the MMIB in a cross-transesterification for conversion of MAA to MMA at least partial conversion of dimeric methacrolein and the corresponding di-MAL ester to MMA and methacrolein
maximum degree of recycling of by-products
maximum cleanliness of disposal streams or offgases

PROBLEM

The problem addressed by the present invention in view of the prior art was therefore that of providing a technically improved process for oxidative esterification of methacrolein which is not affected by the disadvantages of conventional processes and leads to higher yields compared to the prior art.

A particular problem addressed by the present invention was that of providing an improvement in the workup of the crude product from an oxidative esterification of methacrolein and methanol to afford MMA and thus to improve the overall yield of such a process compared to the prior art.

A further problem addressed was that of isolating as many by-products as possible that are formed in the process, especially alkyl methoxyisobutyrate and methacrylic acid, to a maximum degree and providing them in a yield-enhancing manner for the preparation of alkyl methacrylates. A further explicit problem addressed by the invention was that of finding a process that makes it possible to convert several of these by-products if possible in a single process step to give MMA, and preferably builds on process steps that are needed anyway for the isolation of MMA in the workup of the crude product. More particularly, this relates to a solution to the problems based on columns, phase separators, extractors or general equipment already present for other reasons.

A further particular problem addressed was that of providing a process that can be operated with a lowest possible disposal cost, in particular through reduced generation of organic constituents and acids in the waste stream.

SOLUTION

These objects are achieved by a process for preparing alkyl methacrylates in which methacrolein is prepared in a first reaction stage in a reactor I and this is oxidatively esterified with an alcohol, preferably with methanol, in a second reaction stage in a reactor II to give an alkyl methacrylate, preferably correspondingly to give MMA, wherein the process has the feature in accordance with the invention that a, the reactor output from reactor II is separated into a fraction containing the predominant portion of the alkyl methacrylate and a second fraction containing methacrylic acid and an alkyl alkoxyisobutyrate (MAIB). In the preferred case that the alcohol is methanol, the MAIB is methyl methoxyisobutyrate (MMIB).

Moreover, the process according to the invention is characterized in that b. this second fraction is converted in a reactor III in such a way that further alkyl methacrylate is formed from the MAIB and the methacrylic acid. The chemical conversions are shown in Scheme 3, showing, by way or example, the reaction using MAA and MMIB:

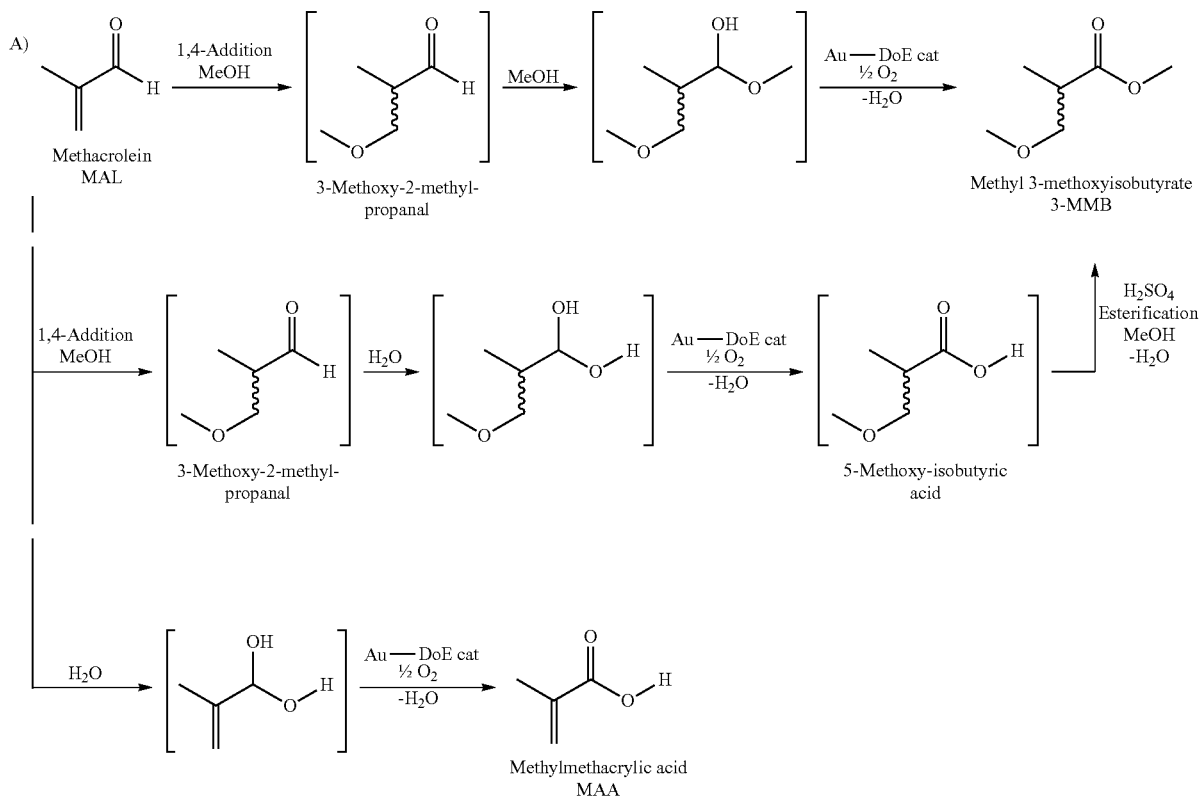

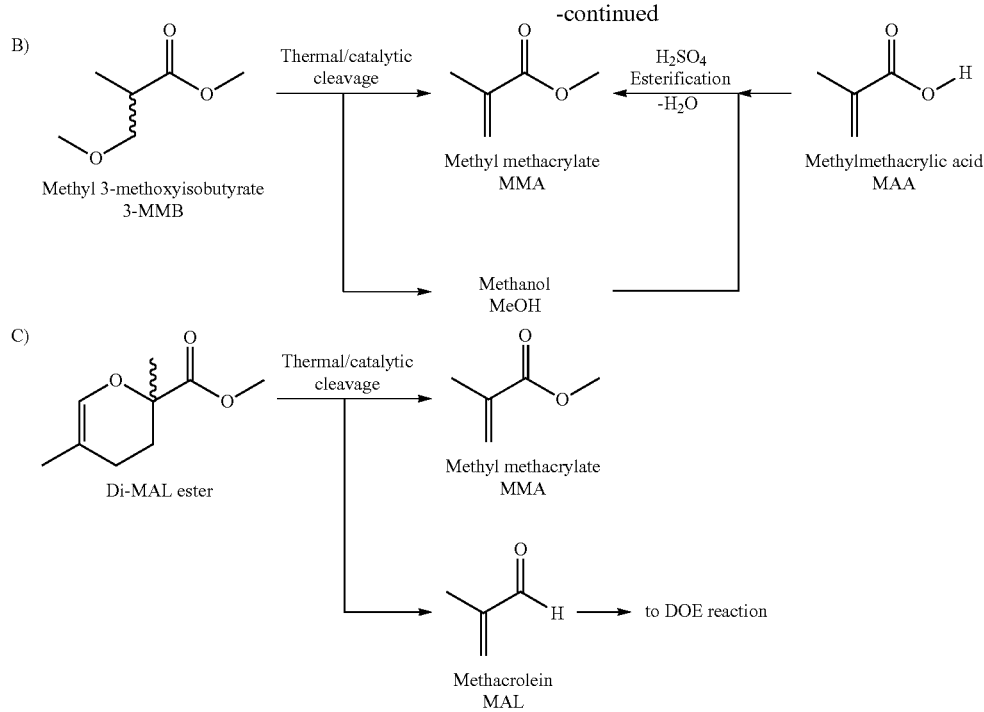

Very advantageously, it can be shown here that the cleavage of one by-product (MMIB) releases methanol, which is required for the purposes of a cross-transesterification to convert the second by-product, namely methacrylic acid MAA, to form MMA, 3-Methoxyisobutyric acid which is formed in traces is also converted in this reaction, first to 3-MMIB and then to MMA.

All these reactions proceed synchronously, preferably in a single apparatus or a single reactor, such that a multitude of by-products are ultimately converted to the MMA target product.

The process for synthesizing MMA which comprises the two above-cited reaction stages may be read up on in U.S. Pat. Nos. 5,969,178, 7,012,039 and WO 2014/170223 in particular. A possible flow diagram according to the invention is shown in the FIGURE.

The first stage of the process for synthesizing the methacrolein is freely choosable according to the invention. The process according to the invention is applicable to a first stage synthesis based either on tert-butanol or isobutylene or on propanal and formalin.

In the preparation of methacrolein based on propanal and formalin as well, there are two possible process variants in principle, which lead in accordance with the invention to a quality of the methacrolein that can be used in the DOE reaction. First of all, propanol and formalin can be converted in a stirred or circulation-pumped reactor at temperatures of 20° C. to 120° C. at pressures of 1 bar to 10 bar. This requires reaction times greater than 10 min to achieve adequate conversions. Secondly, MAL can be prepared from these reactants, and the reaction, at a moderate pressure between 10 and 100 bar at relatively high temperatures between 120° C. and 250° C., achieves desirable high yields with a reaction time of 2 seconds to 20 seconds.

It is preferable when the oxidative esterification is carried out in the liquid phase at a pressure of 2 to 100 bar, preferably at a pressure in the range from 2 to 50 bar, and a temperature in the range from 10° C. to 200° C. with a heterogeneous catalyst. The heterogeneous catalyst generally comprises supported gold-containing nanoparticles having a particle size less than 20 nm, preferably between 0.2 and 20 nm. The reaction stage (A) may comprise an optional and less preferred distillation column II for removal of low-boilers, such as remaining propanal, and/or of high boilers, such as dimeric methacrolein.

More preferably, in step a., the separation is effected by means of at least one extraction and/or a distillation. It is also possible here to use multiple distillation steps or extraction steps, and also combinations of at least one distillation and at least one extraction.

It has been found to be very particularly preferred in the process according to the invention to conduct the process in such a way that the reactor output from reactor II is freed of methacrolein and partly of the alcohol in a first distillation column, giving a stream comprising alkyl methacrylate, water, an alkali metal methacrylate and/or methacrylic acid, MMIB and alcohol. Subsequently, this stream is admixed with a strong acid and separated in an extraction into a hydrophobic phase comprising alkyl methacrylate, MAA and MMIB, and a hydrophilic phase comprising water, the alcohol, and remaining relatively small amounts of main products and by-products from the reaction.

Alternatively and equally preferably, the process according to the invention is executed in such a way that the reactor output from reactor II is freed of methacrolein and partly of the alcohol in a first distillation column, giving a stream comprising alkyl methacrylate, water, an alkali metal methacrylate and/or methacrylic acid, MMIB and alcohol. At this point in the process, the methacrylic acid may be in the form of the free organic acid or of the alkali metal salt or in the form of a mixture of free acid and alkali metal salt. Optionally, by acidification, for example admixing of the mixture with a Brønsted acid, the acid in salt form is converted to the free acid.

This stream is subsequently subjected to an extraction, resulting in an organic phase containing mainly MMA, but also a proportion of the organic by-products MAA and MMIB.

The organic phase that results after extraction is separated in a second distillation into a low-boiling phase comprising alkyl methacrylate and the alcohol, and a high-boiling phase comprising water, MMIB and methacrylic acid.

Thus, in the process according to the invention, separation of the MMA value from the by-products from the DOE reaction, especially in reactor II, is particularly advantageous. More particularly, it is thus surprisingly possible in accordance with the invention to implement separation of the MMA from MAA, MMIB, DIMAL and DIMAL ester and the isomers of HIBA.

This above-described high-boiling phase is then, in the second aspect of the invention, subjected to a further reaction, wherein the by-products of the DOE are converted to the desired main MMA product. The MMA additionally formed in reactor III significantly increases the overall yield of the process. Advantageously, the crude MMA product obtained in reactor III is sent to one or more workup columns in the main process.

The conversion in reactor III is in turn preferably effected at a temperature of at least 90° C., more preferably of at least 110° C. most preferably between 120° C. and 170° C. Thus, the reaction can be conducted purely thermally without addition of a catalyst. More preferably, the reaction is effected thermally in the presence of a catalyst, which may especially be a Brønsted acid.

In a third alternative, the conversion can also be effected in the presence of such a catalyst at temperatures below 130° C. it is more preferable when the Brønsted acid is a strong acid. In accordance with the invention a strong acid is to be understood as meaning an acid stronger than methacrylic acid. This means that this acid has a smaller $pK_A$ than methacrylic acid under standard conditions. A particularly preferred inorganic acid is in this case sulfuric acid. The less preferred organic acids may be, for example, methanesulfonic acid or toluenesulfonic acid. An example of a further suitable mineral acid is phosphoric acid. Sulfuric acid has been found here to be a particularly suitable catalyst. In general, it is advantageous to use a catalyst acid in reactor III which is identical to the acid which is used for acidification and release of the MAA from the alkali metal methacrylate. A third function of the acid in this process is the destruction of troublesome acetals of methacrolein. It is thus possible in the best case to manage with just a single acid within the integrated system. A particularly suitable example of such a universally usable acid is sulfuric acid having different concentration or dilution according to the use function.

It has further been found to be preferable to combine the reactor output from reactor III with the alkyl methacrylate-containing fraction obtained after removal of the MMIB and the methacrylic acid for further workup. This second fraction here may be that after the inventive separation in process step a), not the MMIB-containing stream. However, it is more favourable first to purify this stream in one or more steps before the two fractions are combined for further purification. The choice of preliminary purification depends, for example, on the process chosen for the first process step in reactor I and the raw materials used therein. This preliminary purification of the actual crude alkyl methacrylate may, for example, be a high boiler column, a low boiler column or both distillations connected in series. Alternatively or in parallel, it is of course also possible first to prepurify the reaction output from reactor III before this fraction is combined with the aforementioned other fraction. This purification may also be one or more extractions or distillations or combinations thereof. For this purpose, the acid used, which is obtained from the purification, can optionally be recycled back into reactor III. More preferably, there is a distillation column for removal of MAL directly downstream of reactor II. This can then be recycled into the reactor II or an upstream purification step.

The process that forms one aspect of the present invention is the preparation of methacrolein in the reactor I described. A good overview of the methods and processes for preparation of methacrolein is given by Ullmanns Encyclopedia of industrial chemistry, 2012, Wiley-VCH Verlag GmbH, Weinheim, DOI: 10.1002/14356007.a01_149.pub2.

We have been able to show that multiple process variants are suitable in principle for preparing methacrolein, which can be summarized by way of example as follows:

a. Preparation of methacrolein from propanal and formalin in the presence of catalysts, preferably homogeneous acids, mineral or organic, and organic amines under elevated absolute pressure of greater than 2 bar. Examples are described inter alia in EP 2 998 284 A1 or in U.S. Pat. No. 7,141,702, JP 3069420, JP 4173757. EP 0 317 909 or U.S. Pat. No. 2,848,499. The process according to DE 32113681 is also suitable, where high conversions and yields are achieved with residence times in the range of seconds. The latter publication, however, also makes reference to the production of dimeric methacrolein ("DIMAL"), which ultimately constitutes a loss. These processes proceed at elevated temperatures and pressures with the advantage of a short residence time of the reactants and hence comparatively small reactor volumes.

b. U.S. Pat. No. 4,408,079 is an example, contrasting with the aforementioned processes, of operations at comparatively low temperatures and with much longer residence times, which thus require higher reactor volumes. These processes are conducted at absolute pressures of more than 2 bar. At the same time, however, much greater amounts of catalyst—in some cases of even 50 mol %—are required, but the catalyst solutions can also be recycled. Typically, in these process variants, stirred or circulation pumped stirred tanks or cascades of said tanks are used. A characteristic feature in this process variant is comparatively higher DIMAL contents as by-product, which is attributable to longer residence times and hence increased occurrence of Diels-Alder reaction of methacrolein.

c. The third process variant for preparation of methacrolein is characterized in that isobutene or tert-butanol is reacted in the gas phase over a heterogeneous catalyst with steam and oxygenous gases at temperatures of more than 300° C. and then isolated. A multitude of sub-variants and usable catalyst systems and isolation options is described in the relevant prior art. A good overview in this regard is given by the following reference: Trends and Future of Monomer-MMA Technologies, K. Nagai & T. Ui, Sumitomo Chemical Co., Ltd., Basic Chemicals Research Laboratory, 2005, http-/www.sumitomo chem.co.jp/english/rd/report/theses/docs/20040200_30a.pdf. These processes with C4 raw materials are conducted on the industrial scale in the Asian region in particular.

It is preferable that the first reaction stage in reactor I is a reaction of propanal with formalin. In this case, it is then further preferable that the reactor output from reactor II is freed of methacrolein and partly of the alcohol in a first distillation column, giving a stream comprising alkyl methacrylate, water, an alkali metal methacrylate and/or methacrylic acid, MMIB and alcohol. This stream is then subsequently separated in a second distillation into a light phase comprising alkyl methacrylate and the alcohol and a heavy phase comprising water, MMIB, methacrylic acid, dimeric methacrolein and optionally an alkyl ester of dimeric methacrolein.

The dimeric methacrolein in reactor III in this process variant can then be cleaved to methacrolein. In that case, it is also possible to cleave the optionally present alkyl ester of dimeric methacrolein to methacrolein and the alkyl methacrylate corresponding to the alcohol used. The methacrolein thus obtained in each case can then be separated from the alkyl methacrylate in a later distillation stage and returned to reactor II.

As an alternative to the process variant described, in which the first reaction stage in reactor I is a reaction of propanal with formalin, this first reaction stage may also be an oxidation of tert-butanol and/or isobutene.

In such a variant, it is then particularly preferable to free the reactor output from reactor II in a first distillation column of methacrolein and partly of the alcohol. This affords a stream comprising alkyl methacrylate, water, an alkali metal methacrylate and/or methacrylic acid, MMIB and alcohol. This stream is typically first treated with acid, for example mineral acids, for instance sulfuric acid, wherein the majority of the alkali metal methacrylate is neutralized and hence the free methacrylic acid is formed.

This stream is then subsequently separated in a second distillation and/or an extraction into a light or hydrophobic phase comprising alkyl methacrylate and the by-products from the reaction, namely the majority of the methacrylic acid formed, MMIB, and also DIMAL, DIMAL ester and relatively small amounts of water and methanol, and a heavy hydrophilic phase. This second, predominantly aqueous phase naturally contains few organic products and consists mainly of water and methanol, and contains alkali metal or alkaline earth metal salt from the neutralization.

As one aspect of the present invention, methacrolein is converted in the presence of an oxygenous gas at moderate temperatures between 20 and 150° C. at moderate pressures between 1 and 20 bar in the presence of a heterogeneous spherical precious metal catalyst. A multitude of catalysts can be used for this oxidative esterification of MAL with methanol to give MMA:

The first known use of the direct oxidative esterification of MAL with methanol to give MMA was conducted by Asahi with a Pd—Pb catalyst present on an oxidic support. U.S. Pat. No. 6,040,472 describes these catalysts, but these lead to MMA with only inadequate activities and selectivities by comparison. In this case, the catalysts are Pd/Pb-containing catalysts having a shell structure. The selectivities for MMA are reported to be up to 91%, and the space-time yield is reported to be up to 5.3 mol. Here too, lead doping is crucial for the formation of the active oxidation species, but creates the above-described disadvantages through creeping loss of lead ions. By-products of these catalysts, as in all other systems too, are methacrylic acid and other by-products.

EP 1 393 800 describes gold-containing catalysts, wherein the catalytic gold particles described as active oxidation species must especially have an average diameter of less than 6 nm. Said gold particles are distributed over a silicon oxide support or a $TiO_2/SiO_2$ support. As additional active components as well as the gold, such catalysts also contain, inter alia, other metals in oxidic form. A synergistic and activity- and selectivity-enhancing effect is ascribed to these doping components. Preparation is effected by applying the gold salt and further metal salts to an oxidic support.

Haruta et al. in J. Catal. 1993, Vol. 144, pp 175-192 state that gold nanoparticles applied to transition metal oxide supports, such as $TiO_2$, $Fe_2O_3$ or $Co_3O_4$, are active oxidation catalysts. In this case, an interaction between gold and transition metal plays a crucial role for the catalyst activity.

EP 2 177 287 and EP 2 210 864 describe nickel-containing catalysts with shell structure. Selectivity for MMA in the case of these catalysts is up to 97%. The space-time yield is described as 9.7 mol of MMA/(kg h) with a gold content in the catalyst of about 1% by weight. According to examples, an $NiO_x$/Au catalyst shows much better activities and selectivities for MMA, while other combinations, for example Au with CuO or else $Co_3O_4$, are much less active and selective. In principle, this is a further development of the above-described catalysts, wherein the inhomogeneous distribution of the gold-Ni oxide composite particle and an inactive catalyst shell characterize these new catalysts. In these too, reference is made to the formation of methacrylic acid as by-product.

EP 2 210 664 discloses a catalyst having, in the outer region, in the form of what is called an eggshell structure, nickel oxide and gold nanoparticles on a support composed of $SiO_2$, $Al_2O_3$ and a basic element, especially an alkali metal or alkaline earth metal. The nickel oxide is enriched at the surface, but is also present in lower concentrations in deeper layers of the catalyst particle.

WO 2017/084969 A1 describes catalyst systems based on two or more mixed oxides as carrier, which likewise include nanoparticulate gold as well as cobalt oxide as active component. The distribution of the catalytically active components, namely gold and cobalt, is in anisotropic distribution across the cross section of the grain. Further newer catalysts for said reaction are described in U.S. Pat. No. 9,676,699. Similar carrier systems based on silica, alumina, alkaline earth metal oxide mixtures are described here, which include palladium as well as bismuth with further third-element dopants. Here too, reference is made to the correlation between the water concentration and the methacrylic acid that forms as by-product.

Thus, the difference in these catalyst systems with regard to the support materials used is similar to the degree of difference in the preparations thereof and ultimately also the performance with regard to conversion and selectivity. Nevertheless, all these catalyst systems lead to similar by-product characteristics. A common factor to all catalysts is that, in steady-state operation, as well as the desired alkyl methacrylate, there is also formation of greater or lesser amounts of methacrylic acid, alkoxyisobutyric esters (MAIB), and dimers of the methacrolein used and alkyl esters of these dimers. Additionally formed are further by-products such as hydroxyisobutyric acid and the corresponding esters thereof. These by-products are of particular relevance since they are high-boning relative to the desired alkyl methacrylate, and accumulate and ultimately collect in high-boning fractions relative to MMA in the course of workup.

LIST OF REFERENCES FOR THE FIGURE

The FIGURE is an example of a possible flow diagram of the MMA process according to the invention including a reactor for obtaining MMA from MMIB and MA.

(1) Reactor I for MAL synthesis
(2) Distillation column
(3) Reactor II for DOE reaction
(4) MAL removal
(5) Intermediate column and/or extraction
(6) Column for methanol removal
(7) Column for MMA purification—high boilers
(8) 2nd column for MMA purification—low boilers
(9) 3rd column for MMA purification—purifying column
(10) Purified MMA
(11) Optional column for reduction in the amount of MMA from bottom stream from (7)
(12) Addition of acid and MeOH for (13)
(13) Reactor III for cleavage of MMIB to MMA and DIMAL ester to MAL and MMA and esterification of MAA to MMA
(14) Optional column for separation of the values from high boilers & sulfuric acid
(15) Wastewater
(16) Recycling for methacrolein and methanol

EXPERIMENTAL

Example 1: Performance of the Reaction at Standard Pressure as a Fed Batch with Fresh Reactants, MAA and MMIB The reaction is conducted in a glass three-neck flask with attached column.

The three-neck flask is equipped with a precision glass stirrer and with a 1 n-high column having a clear diameter of 40 mm; the heating is by means of an oil bath. The column is filled with Raschig rings; a reflux divider is placed at the top of the column section in order to be able to control reflux and removal. A 1 1 3-neck flask is initially charged with 2 mol of MMIB and 2 mol of methacrylic acid, and 0.2 mol of water.

Added to this mixture in each case are 200 ppm of phenothiazine and 50 ppm of Tempol as stabilizers and for inhibition of any free-radical polymerization of (meth)acrylic reactants and products under the reaction conditions. The reaction mixture is heated to 150° C. by means of an oil bath; after 10 min, this temperature has been attained with the preheated oil bath; the column is switched to full reflux, such that no distillate is obtained at first. On attainment of the internal temperature of 150° C., a mixture of MMIB, MAA and MeOH, water and sulfuric acid is continuously fed into the reaction mixture via the immersed capillary at a metering rate of 150 g/h. The feed mixture is metered in by means of an HPLC pump; a second HPLC pump removes the reaction bottoms that arise through a capillary once the reaction has run to a steady state.

Reactants and catalyst, alcohol and water are premixed separately and introduced into the reaction via a capillary which is guided to beneath the stirrer. Composition of the reed mixture:

TABLE 1

Feed mixture for cleavage of MMIB to MAA with parallel esterification of MAA to MMA

| Chemical | % by wt. | M [g/mol] | Feed [g/h] | Feed [mol/h] | Mol % [basis = MMIB] |
|---|---|---|---|---|---|
| MMIB | 44 | 118 | 66 | 0.56 | 100 |
| MAA | 32 | 86 | 48 | 0.56 | 100 |

TABLE 1-continued

Feed mixture for cleavage of MMIB to MAA with parallel esterification of MAA to MMA

| Chemical | % by wt. | M [g/mol] | Feed [g/h] | Feed [mol/h] | Mol % [basis = MMIB] |
|---|---|---|---|---|---|
| Water | 3.3 | 18 | 4.95 | 0.28 | 49 |
| Sulfuric acid | 3.7 | 98 | 5.55 | 0.06 | 10 |
| Methanol | 17 | 32 | 25.5 | 0.80 | 142 |

Thus, the molar ratio of the $C_4$ by-products MAA and MMIB is 1:1. The water content is 49 mol % based on MMIB and 142 mol % of MeOH based on MMIB.

The oil bath is heated up to 160° C. with commencement of addition of the feed; the internal temperature in the reactor rises gradually up to about 150° C. and a mixture consisting of the azeotropic compositions of the binary MeOH and MMA/MMA and water azeotropes collects at the top of the column. As soon as the top of the column has reached a stable temperature of 69° C., a reflux ratio of 0.8 is established and distillate is removed.

The reaction is operated continuously at first for 6 h, with quantification and analysis of the amount of distillate every hour. The plant is operated such that an average of about 90% of the mass of reactants supplied per hour is drawn off as distillate at the top of the column, while the reaction bottoms are likewise discharged continuously; an average of about 10% of the feed stream supplied is removed by means of an HPLC pump. On average, the fill level in the flask is thus maintained and the reaction can be considered as being steady-state in terms of volume or mass at this stage. Connected downstream of the condenser, which is operated with tap water having a cooling water temperature of about 18° C., at the top of the column is a cold trap in order to capture volatile components; the cold trap is operated with a mixture of acetone/dry ice at nearly minus 60° C.; the cold trap is filled with THF in order to absorb and qualitatively elucidate and determine volatile components.

The liquid phase at first turns yellow, then light orange within 6 h; barely any rise in viscosity is perceptible.

The top product from the column obtained as distillate in the steady state weighs 134.9 g/h and, by GC chromatography, has the following composition:

TABLE 2

Distillate product of the reaction

| Chemical | % by wt. | M [g/mol] | Distillate [g/h] | Distillate [mol/h] |
|---|---|---|---|---|
| MMA | 79.1 | 100 | 106.7 | 1.06 |
| Water | 3.3 | 18 | 4.7 | 0.26 |
| Methanol | 17.6 | 32 | 23.7 | 0.74 |
| Total distillate | 100 | # | 134.9 | 2.06 |

The bottom product obtained from the discharge in the steady state weighs 15.1 g/h and has the following composition:

TABLE 3

Bottom product from the reaction

| Chemical | % by wt. | M [g/mol] | Bottoms [g/h] | Bottoms [mmol/h] |
|---|---|---|---|---|
| MMIB | 17.5 | 118 | 2.64 | 22.4 |
| MAA | 21.9 | 86 | 3.30 | 38.4 |
| Methanol | 0.1 | 32 | 0.01 | 0.3 |
| Sulfuric acid | 36.8 | 98 | 5.55 | 56.6 |
| Water | 1.7 | 18 | 0.25 | 13.9 |
| High boilers | 22.2 | # | 3.35 | # |
| Total bottoms | 100 | # | 15.1 | # |

In terms of the amounts of reactant supplied, this corresponds to a theoretical yield of MMA based on MMIB of 96%, based on the methacrylic acid esterified to MMA of 95% and a methanol recovery rate of 93%.

In the cold trap, as well as the THF solvent used as absorbent, small amounts of dimethyl ether are detected by means of gas chromatography (boiling point −24° C.).

The experiment shows that, under the conditions chosen, it is possible to use mixtures comprising MAA and MMIB, in the presence of stoichiometric amounts of sulfuric acid and in the presence of MeOH and water, to prepare crude MMA with high efficiency and at high conversion rates (based on the reactants).

Examples 2 to 9

Preparation of methacrolein from propanal and formalin: methacrolein was prepared and isolated according to EP 2 998 284.

A formalin solution having a formalin content of 37% by weight or 55% by weight, depending on the example, and propanal are mixed by means of a static mixer (referred to below as aldehyde solution) and the mixture is subsequently heated to the desired temperature (see Table 1) in an oil-heated heat exchanger. The exact water content of the formalin, depending on the example, plays no further role, since this completely enters the water content of the fresh feed in accordance with Table 1. A recycle stream, which adjoins the tubular reactor from the bottom of the product column, is mixed with acetic acid and dimethylamine (as 40% solution in water) and is likewise pre-heated to the desired temperature. The pre-heated aldehyde solution and the pre-heated catalyst solution are mixed in a further static mixer. This reactant mixture is then fed to an oil-heated tubular reactor. The reaction is typically carried out at pressures of about 35 to 40 bar.

The product mixture at the outflow of the tubular reactor is released via a valve and enters the product column for the distillation. At the top of this column, after condensation and phase separation, a biphasic mixture of methacrolein and an aqueous phase is obtained. The aqueous phase is fed back to the column. The organic phase enters the product container. At the bottom of the column, a partial stream is fed back into the reaction as recycling. Another partial stream is removed as aqueous product into a further product container. In examples 1 to 4, a methacrolein quality having a DIMAL content of less than 0.2% by weight is obtained. The water content is about 56% by weight and the dimethylamine content, based on the water in the feed, is about 2.7% by weight. The temperature in the reactor is between 122° C. as inlet temperature and 153° C. as outlet temperature. No significant temperature spike occurs.

Examples 5 to 7 show that the parameters of the reaction regime have a crucial effect on conversion and DIMAL content, since it was possible here to achieve a content of dimeric MAL below 0.4% by weight, but not below 0.2% by weight. The difference from examples 1 to 4 here is in particular the higher maximum temperature and outlet temperature, as well as a higher inlet temperature in some cases.

Examples 8 and 9 show embodiments that produce a methacrolein quality having a content of dimeric MAL below 0.5% by weight. Here, the inlet temperatures and particularly the maximum temperatures were even higher. More particularly, the maximum temperatures were above the preferred maximum temperatures of 165° C. or even 170° C.

TABLE 4

Preparation of MAL from propionaldehyde and formalin
Table: Preparation of methacrolein from propanal (PA) and formalin (FO)

| | PA:FO | DMA:PA | ACOH:DMA | Recycle | DMA:PA | H$_2$O | DMA/H2O |
|---|---|---|---|---|---|---|---|
| | Fresh feed | | | | Reactor inlet | | |
| | mol/mol | mol % | mol/mol | % | mol % | % | % |
| DE3213681A1 Ex. 1 | 1 | 3.7 | 1.08 | — | — | 50 | 1.8 |
| DE3213681A1 Ex. 2 | 1 | 3.6 | 1.14 | — | — | 40 | 2.5 |
| Example 1 | 0.99 | 2.50 | 1.09 | 70.5 | 7.8 | 55.6 | 2.74 |
| Example 2 | 0.99 | 2.51 | 1.09 | 71.0 | 7.8 | 56.1 | 2.74 |
| Example 3 | 0.98 | 2.61 | 1.09 | 71.2 | 8.2 | 54.9 | 2.82 |
| Example 4 | 0.96 | 2.51 | 1.09 | 70.1 | 7.7 | 56.5 | 2.71 |
| Example 5 | 0.99 | 2.51 | 1.09 | 70.5 | 7.8 | 55.7 | 2.75 |
| Example 6 | 0.99 | 2.51 | 1.09 | 70.4 | 7.8 | 55.6 | 2.75 |
| Example 7 | 0.98 | 2.50 | 1.09 | 70.5 | 7.7 | 56.0 | 2.72 |
| Example 8 | 0.99 | 2.51 | 1.09 | 70.5 | 7.8 | 55.6 | 2.74 |
| Example 9 | 0.99 | 2.52 | 1.08 | 70.4 | 7.8 | 55.6 | 2.76 |

| | RT sec | T$_{OIL}$ ° C. | T$_{in}$ ° C. | T$_{max}$ | T$_{out}$ ° C. | PA conversion % | Selectivity MAL % | c DIMAL % |
|---|---|---|---|---|---|---|---|---|
| DE3213681A1 Ex. 1 | 6.9 | | 161 | 184 | — | 99.5 | 98.1 | 0.49 |
| DE3213681A1 Ex. 2 | 6 | | 162 | 205 | — | >99.4 | 97.2 | <1 |
| Example 1 | 9.30 | 139.5 | 122.5 | 152.6 | 152.2 | 99.37 | 98.75 | 0.18 |
| Example 2 | 9.26 | 139.1 | 122.5 | 152.3 | 152.0 | 99.30 | 98.85 | 0.18 |

TABLE 4-continued

Preparation of MAL from propionaldehyde and formalin
Table: Preparation of methacrolein from propanal (PA) and formalin (FO)

| Example 3 | 9.41 | 139.9 | 122.1 | 152.3 | 152.2 | 99.35 | 98.67 | 0.18 |
| Example 4 | 9.21 | 139.1 | 122.8 | 153.0 | 153.0 | 99.46 | 98.33 | 0.18 |
| Example 5 | 9.26 | 143.9 | 129.9 | 160.2 | 155.5 | 99.75 | 98.19 | 0.34 |
| Example 6 | 9.30 | 144.2 | 127.3 | 157.7 | 154.7 | 99.65 | 98.47 | 0.27 |
| Example 7 | 9.22 | 139.0 | 122.5 | 156.3 | 154.9 | 99.57 | 98.62 | 0.22 |
| Example 8 | 9.26 | 159.8 | 142.1 | 173.0 | 169.1 | 99.67 | 98.03 | 0.49 |
| Example 9 | 9.26 | 146.4 | 133.8 | 165.4 | 159.7 | 99.77 | 98.34 | 0.45 |

The methacrolein prepared as described above is decompressed after the reaction (optionally partly evaporated in a flash box), and guided into a distillation column. At the top of the distillation column, after condensation, a biphasic mixture is obtained (depending on the temperature, a greater or lesser water phase separates out), where the upper phase contains methacrolein quality of >97%, with a water content of 1-3 wt %. The formalin content in the methacrolein is <2000 ppm; the methanol content, depending on the methanol content of the formalin used, is between 0.1 and 1.0 wt %. According to the above examples, the methacrolein contains a DIMAL content of 0.18 wt % to <1 wt %. This quality is used in the experiments which follow for direct oxidative esterification with methanol.

Example 10: Performance of Direct Oxidative Esterification in the Liquid Phase A 20 l reactor with a sparging stirrer is charged with a reaction mixture composed of 38 percent by weight of methacrolein in methanol with a slurry density of 8 percent by weight of catalyst. The reaction mixture is brought to 5 bar while stirring at 80° C., and air is metered in such that the oxygen concentration in the tail gas downstream of the condensers is 4.0 percent by volume. The pH is adjusted to 7 by continuously introducing 4 percent by weight NaOH in methanol solution. The reaction mixture is removed continuously from the reactor in such a way that the catalyst hourly space velocity is 11 mol MAL/kg catalyst/hour. The run time is in each case 1000 hours.
  a) The catalyst used is a gold-cobalt oxide catalyst (WO2017084969 A1) and a conversion of 78% MAL is obtained at a selectivity of 94.1% MMA. The selectivity for MAA is 3.1% and the selectivity for MMIB 1.2%.
  b) The catalyst used is a gold-nickel oxide catalyst (U.S. Pat. No. 8,450,235) and a conversion of 75% MAL is obtained at a selectivity of 94.4% MMA. The selectivity for MAA is 2.5% and the selectivity for MMIB 1.2%.
  c) The catalyst used is a palladium-lead catalyst (U.S. Pat. No. 5,969,178), where the pH of the reaction is adjusted to 6.3, and a conversion of 60% MAL is obtained at a selectivity of 89% MMA. The selectivity for MAA is 7% and the selectivity for MMIB is below 0.1%.
  d) The catalyst used is a palladium-bismuth-tellurium catalyst (US20160188072) and the conditions and stoichiometries are set according to examples 2 and 3 as described in US20160188072. A conversion of 89% is obtained at a selectivity of 92% MMA. The selectivity for MAA is below 0.2% and the selectivity for MMIB is 1.2%.

Example 11: Cleavage of MMIB to MMA and Methanol with Simultaneous Esterification of MAA to MMA with Reaction Mixtures from Example 3 after Inventive Removal of Methacrolein and Methyl Methacrylate. Sulfuric Acid as Catalyst The reaction mixture obtained from Example 3a was taken after the workup:
The workup is described by way of example, and the respective compositions are listed in Table 1.
The output from reactor II (1000 g/hr) was guided to the MAL recovery column at plate 11 of 22. The temperature in the bottoms was 70° C. at a pressure of 930 mbar. The bottom stream was acidified to pH 2 with sulfuric acid and separated in a decanter, and the organic phase was run into the bottom of the extraction column, while the aqueous phase was introduced Into the top of the 30-plate extraction column. The bottom temperature of the extraction column was 43.9° C. at a pressure of 1013 mbar. The top stream from the extraction column was introduced to plate 6 of 10 in the high boiler column. The bottom temperature was 85.4° C. at a pressure of 235 mbar.

TABLE 5

Composition of the reaction mixture in the different workup steps

| Component | Reactor output | Bottoms of MAL recovery | Tops from extraction | Liquid phase of high boilers |
|---|---|---|---|---|
| Methanol | 47.3% | 28.9% | 1.8% | 22 ppm |
| Water | 5.6% | 10.9% | 6.0% | 0.3% |
| MAL | 10.3% | 64 ppm | 1300 ppm | 12 ppm |
| MMA | 32.6% | 55.1% | 83.4% | 11.4% |
| MMIB | 0.4% | 1.2% | 1.4% | 32.2% |
| MAA | 0.9% | 0.6% | 2.8% | 24.6% |
| DIMAL ester | 0.1 | 0.3% | 0.7% | 12.8% |
| Secondary components | 2.8% | 2.1% | 3.8% | 19.0% |

The liquid phase from the high boiler column was collected and used for the cleavage of MMIB to MMA and MeOH, and of DIMAL ester to MAL and MMA, with simultaneous esterification of MAA with MeOH to give MMA.
A 500 ml three-neck flask was provided with a column and a glass thermometer. At the top of the column, 50 g of MeOH with phenothiazine (about 500 ppm) were placed in a dropping funnel in order to prevent polymerization in the column by continuous addition. The thermocouple was placed into the oil bath (T(oil)=165° C.).
300 g of feed (1 eq., 0.73 mol 3-MMib; 1.17 eq., 0.85 mol MAA; 0.34 mol MMA, 0.23 mol DIMAL ester),
2.84 g (0.04 eq., 0.029 mol) of $H_2SO_4$ and
13.42 g of H2O (1.02 eq., 0.75 mol)

were initially charged in the three-neck flask which was guided into the oil bath (target temperature=165° C.).

The mixture was heated to 165° C. (oil bath target temperature) for 3 h, reaching a bottom temperature of 151° C. The distillate was removed continuously and analysed by HPLC. Over the course of the reaction of 3 hours, the methanol/stabilizer solution (6.54 g/h, 0.20 mol was added.

Table No. 2 below shows the amounts of sulfuric acid, water, methanol and feed sample used. Also listed is the composition of the feed sample for 3-MMib, MAA and MMA together with the molar masses.

TABLE 6

Amount of the substances used and their molar masses

|  | Feed [% by wt.] | H₂SO₄ [% by wt.] | H₂O [% by wt.] | MeOH [% by wt.] | Stab. [% by wt.] | Total [g] | Mol. mass |
|---|---|---|---|---|---|---|---|
| 3-MMib | 32.31 |  |  |  |  |  | 132.16 |
| MAA | 24.61 |  |  |  |  |  | 86.09 |
| MMA | 11.41 |  |  |  |  |  | 100.12 |
| DIMAL ester | 12.8 |  |  |  |  |  | 170.21 |
| H2SO4 |  | 98.00 |  |  |  |  | 98.08 |
| H2O |  | 2.00 | 100.00 |  |  |  | 18.02 |
| MeOH |  |  |  | 100.00 |  |  | 32.04 |
| S47 |  |  |  |  |  |  |  |
| S71 |  |  |  |  |  |  |  |
| Masses [g] | 300.51 | 2.84 | 13.42 | 19.63 | 0.26 | 362.57 |  |

Table No. 7 shows the recovery of the masses of the above-listed reactants used.

TABLE 7

Conclusion of mass balance

| Amount used [g] | Distillate [g] | Bottoms [g] | Dist. + bottoms [g] | Difference [g] | Mass balance |
|---|---|---|---|---|---|
| 362.57 | 232.81 | 125.78 | 358.59 | 3.98 | 98.90% |

The mass balance is at a recovery rate of 98.90%. Table No. 8 shows the molar distribution of the components in distillate and bottoms.

TABLE 8

Distribution of the components in distillate and bottoms

| Comp. | Initial charge [mol] | Dist. [mol] | Bottoms [mol] | Delta mol | Conversion/sel. |  |
|---|---|---|---|---|---|---|
| 3-MMIB | 0.735 | 0.000 | 0.029 | 0.705 | 96.00% | Conversion of 3-MMIB |
| MAA | 0.859 | 0.001 | 0.108 | 0.750 | 87.30% | Conversion of MAA |
| MMA | 0.342 | 1.620 | 0.166 | 1.443 | 99.16% | Selectivity/(MAA + 3-MMIB) |
| MAL | 0 | 0.019 | 0 | 0.019 | 8.26% | Conversion of DIMAL ester to MAL and MMA |
| MeOH(*) | 0.613 | 0.23 |  | — | — |  |
| H2O | 0.753 |  |  | — | — |  |

The experiment was successful; there was high conversion or 3-MMIB and MAA to MMA.

A conversion of 96.0% 3-MMIB to MMA and 87.3% conversion of MAA to MMA was found. Selectivity for MMA added up to 99.18% for MAA and 3-MMIB. The conversion in the thermal cleavage of DIMAL ester to MAL and MMA was 8.26%.

Example 12: Cleavage of MMIB to MMA and Methanol with Simultaneous Esterification of MAA to MMA with Reaction Mixtures from Example 3 after Inventive Removal of Methacrolein and Methyl Methacrylate. Phosphoric Acid as Catalyst The reaction was conducted analogously to Example 11 and phosphoric acid was used in place of sulfuric acid.

The experiment was successful; there was high conversion of 3-MMIB and MAA to MMA.

A conversion of 94.2% 3-MMIB to MMA and 86.8% conversion of MAA to MMA was found. Selectivity for MMA added up to 99.0% for MAA and 3-MMIB. The conversion in the thermal cleavage of DIMAL ester to MAL and MMA was 8.25%.

Example 13: Cleavage of MMIB to MMA and Methanol with Simultaneous Esterification of MAA to MMA with Reaction Mixtures from Example 3 after Inventive Removal of Methacrolein and Methyl Methacrylate. Methanesulfonic Acid as Catalyst The reaction was conducted analogously to Example 11 and methanesulfonic acid was used in place of sulfuric acid.

The experiment was successful; there was high conversion of 3-MMIB and MAA to MMA.

A conversion of 92.6% 3-MMIB to MMA and 84.7% conversion of MAA to MMA was found. Selectivity for MMA added up to 98.8% for MAA and 3-MMIB. The conversion in the thermal cleavage of DIMAL ester to MAL and MMA was 8.20%.

Example 14: Cleavage of MMIB to MMA and Methanol with Simultaneous Esterification of MAA to MMA with Reaction Mixtures from Example 3 after Inventive Removal of Methacrolein and Methyl Methacrylate. Temperature of 120° C.

The reaction was conducted analogously to Example 11 at a temperature of 120° C.

There was high conversion of 3-MMIB and MAA to MMA.

A conversion of 60.4% 3-MMIB to MMA and 87.3% conversion of MAA to MMA was found. The conversion in the thermal cleavage of DIMAL ester to MAL and MMA was 8.20%.

Example 15: Cleavage of MMIB to MMA and Methanol with Simultaneous Esterification of MAA to MMA with Reaction Mixtures from Example 3 after Inventive Removal of Methacrolein and Methyl Methacrylate. Temperature of 90° C.

The reaction was conducted analogously to Example 11 at a temperature of 90° C.

Conversion of 3-MMIB to MMA was not high, but that of MAA to MMA was.

A conversion of less than 1% 3-MMIB to MMA and 88.0% conversion of MAA to MMA was found.

The thermal cleavage of DIMAL ester to MAL and MMA did not proceed.

Example 16: Cleavage of MMIB to MMA and Methanol with Simultaneous Esterification of MAA to MMA with Reaction Mixtures from Example 3 after Inventive Removal of Methacrolein and Methyl Methacrylate. Increased Amount of Sulfuric Acid The reaction was conducted analogously to Example 11 with an increased amount of sulfuric acid of 40 mol %.

The experiment was successful; there was high conversion of 3-MMIB and MAA to MMA.

A conversion of 95.9% 3-MMIB to MMA and 87.4% conversion of MAA to MMA was found. Selectivity for MMA added up to 99.14% for MAA and 3-MMIB. The conversion in the thermal cleavage of DIMAL ester to MAL and MMA was 8.16%.

Comparative Example 1: Cleavage of MMIB to MMA and Methanol with Simultaneous Esterification of MAA to MMA with Reaction Mixtures from Example 3 after Inventive Removal of Methacrolein and Methyl Methacrylate. Temperature of 23° C.

The reaction was conducted analogously to Example 11 at a temperature of 23° C.

Conversions of 3-MMIB to MMA and of MAA to MMA were not high.

A conversion of less than 1% 3-MMIB to MMA and 20% conversion of MAA to MMA was found. The thermal cleavage of DIMAL ester to MAL and MMA did not proceed.

Comparative Example 2: Cleavage of MMIB to MMA and Methanol with Simultaneous Esterification of MAA to MMA with Reaction Mixtures from Example 3 after Inventive Removal of Methacrolein and Methyl Methacrylate. No Addition of Sulfuric Acid as Catalyst The reaction was conducted analogously to Example 11 without addition of sulfuric acid as catalyst.

Conversion of 3-MMIB to MMA was high, but there was no conversion of MAA to MMA.

A conversion of 94% 3-MMIB to MMA and no conversion of MAA to MMA was found. The thermal cleavage of DIMAL ester to MAL and MMA was 8.0%.

Example 17: Continuous Cleavage of MMIB to MMA and Methanol with Simultaneous Esterification of MAA to MMA with Reaction Mixtures from Example 3 after Inventive Removal of Methacrolein and Methyl Methacrylate The reaction was conducted analogously to Example 11. In addition, on attainment of the bottom temperature of 151° C., a continuous feed of feed mixture of 57 g/hr was commenced. The experiment ran for 8 hours.

The experiment was successful; there was high conversion of 3-MMIB and MAA to MMA.

A conversion of 95.5% 3-MMIB to MMA and 87.5% conversion of MAA to MMA was found. Selectivity for MMA added up to 98.7% for MAA and 3-MMIB. The conversion in the thermal cleavage of DIMAL ester to MAL and MMA was 8.05%.

The invention claimed is:

1. A process for preparing alkyl methacrylates, comprising:
   preparing methacrolein in a first reaction stage in a reactor I, and
   oxidatively esterifying the methacrolein with an alcohol in a second reaction stage in a reactor II to give an alkyl methacrylate, wherein
   a. a reactor output from reactor II is separated into a first fraction containing a predominant portion of the alkyl methacrylate and a second fraction containing methacrylic acid and an alkyl alkoxyisobutyrate, and
   b. the second fraction is converted in a reactor III in such a way that further alkyl methacrylate is formed from the alkyl alkoxyisobutyrate and the methacrylic acid.

2. The process according to claim 1, wherein the separation in step a is effected by at least an extraction and/or a distillation.

3. The process according to claim 1, wherein the reaction in step b is conducted at a temperature equal to or higher than a temperature of the oxidative reaction in reactor II.

4. The process according to claim 1, wherein the reaction in step b is conducted with a reaction mixture comprising the alkyl alkoxyisobutyrate, the methacrylic acid, dimeric methacrolein (DIMAL) as a by-product from reactor II, one or more derivatives of dimeric methacrolein as a by-product from reactor II, water, and free alcohol,
   wherein the free alcohol is optionally added from a separate feed.

5. The process according to claim 1, wherein the second fraction is reacted in reactor III at a temperature of at least 90° C.

6. The process according to claim 1, wherein the second fraction is reacted in reactor III in step b in the presence of a catalyst.

7. The process according to claim 1, wherein step a comprises freeing the reactor output from reactor II of methacrolein and partly of the alcohol in a first distillation column, to obtain a stream comprising:
alkyl methacrylate,
water,
methacrylic acid and/or an alkali metal methacrylate obtained from at least partial neutralization of methacrylic acid with an alkaline or basic auxiliary,
alkyl alkoxyisobutyrate, and
alcohol,
wherein step a then further comprises admixing the stream with a strong acid and separating in an extraction into a hydrophobic phase comprising alkyl methacrylate, a greater fraction of methacrylic acid and alkyl alkoxyisobutyrate, and a hydrophilic phase comprising water, the alcohol, and fractions of alkyl methacrylate and methacrylic acid, and
wherein step a then further comprises separation of the hydrophobic phase into the first fraction containing the predominant portion of the alkyl methacrylate and the second fraction containing the methacrylic acid and the alkyl alkoxyisobutyrate.

8. The process according to claim 1, wherein step a comprises freeing the reactor output from reactor II of methacrolein and partly of the alcohol in a first distillation column, to obtain a stream comprising:
alkyl methacrylate,
water,
methacrylic acid and/or an alkali metal methacrylate obtained from at least partial neutralization of methacrylic acid with an alkaline or basic auxiliary,
alkyl alkoxyisobutyrate, and
alcohol,
wherein the stream is then separated in a second distillation into a light phase comprising alkyl methacrylate and the alcohol as the first phase, and a heavy phase comprising water, alkyl alkoxyisobutyrate and methacrylic acid and/or the alkali metal methacrylate, as the second phase.

9. The process according to claim 1, wherein the alcohol is methanol, the alkyl methacrylate is methyl methacrylate and the alkyl alkoxyisobutyrate is methyl methoxyisobutyrate (MMIB).

10. The process according to claim 1, wherein the reaction in reactor III is effected at a temperature between 80 and 170° C.

11. The process according to claim 6, wherein the catalyst in reactor III is sulfuric acid.

12. The process according to claim 1, wherein the first reaction stage in reactor I is a reaction of propanal with formalin.

13. The process according to claim 1, wherein the first reaction stage in reactor I is a reaction of isobutene and/or tert-butanol with atmospheric oxygen in the presence of a heterogeneous catalyst at temperatures of 300 to 500° C. to form methacrolein, wherein the methacrolein is condensed and worked up to a purity of at least 80% and isolated in liquid form, and wherein the methacrolein is then sent to the further reaction in reactor II of oxidative esterification.

14. The process according to claim 4, wherein step a comprises freeing the reactor output from reactor II of methacrolein and partly of the alcohol in a first distillation column, to obtain a stream comprising:
alkyl methacrylate,
water,
methacrylic acid and/or an alkali metal methacrylate obtained from at least partial neutralization of methacrylic acid with an alkaline or basic auxiliary,
alkyl alkoxyisobutyrate, and
alcohol,
wherein the stream is then separated in a second distillation into a light phase comprising alkyl methacrylate and the alcohol as the first phase, and a heavy phase comprising water, alkyl alkoxyisobutyrate, methacrylic acid and/or the alkali metal methacrylate, dimeric methacrolein and an alkyl ester derivative of dimeric methacrolein, as the second phase.

15. The process according to claim 14, wherein dimeric methacrolein is cleaved in reactor III into methacrolein, and the alkyl ester derivative of dimeric methacrolein is cleaved into methacrolein and the alkyl methacrylate.

16. The process according to claim 15, wherein the methacrolein from reactor III is separated from the alkyl methacrylate in a later distillation stage and returned to reactor II.

17. The process according to claim 16, wherein the heavy phase further comprises terephthalic acid obtained as a by-product, and wherein the terephthalic acid is removed from a reactor output from reactor III as a high-boiling component by distillation or as a hydrophilic component by extraction.

18. The process according to claim 6, wherein the catalyst is a Brønsted acid and wherein, after the second fraction is reacted in reactor III, the catalyst is recycled into reactor III or another workup step.

19. The process according to claim 4, wherein the derivative of dimeric methacrolein is a dimeric methacrolein ester.

20. The process according to claim 6, wherein the second fraction is reacted in reactor III in the presence of a Brønsted acid.

* * * * *